United States Patent
Nemeth et al.

(10) Patent No.: US 7,638,060 B2
(45) Date of Patent: Dec. 29, 2009

(54) PROCESS FOR REMOVING CONTAMINANTS FROM SILICONE-BASED SOLVENTS

(75) Inventors: Laszlo T. Nemeth, Barrington, IL (US); Anil R. Oroskar, Oakbrook, IL (US); Santi Kulprathipanja, Inverness, IL (US); Rusty M. Pittman, New York, NY (US)

(73) Assignee: UOP LLC, Des Plaines, IL (US)

( * ) Notice: Subject to any disclaimer, the term of this patent is extended or adjusted under 35 U.S.C. 154(b) by 179 days.

(21) Appl. No.: 11/782,731

(22) Filed: Jul. 25, 2007

(65) Prior Publication Data

US 2008/0015391 A1 Jan. 17, 2008

Related U.S. Application Data

(60) Division of application No. 11/130,649, filed on May 17, 2005, now Pat. No. 7,329,624, which is a continuation-in-part of application No. 10/918,880, filed on Aug. 16, 2004, now Pat. No. 7,431,843.

(51) Int. Cl.
C02F 3/00 (2006.01)

(52) U.S. Cl. .................................... 210/670; 210/688

(58) Field of Classification Search ......... 210/670–678, 210/688
See application file for complete search history.

(56) References Cited

U.S. PATENT DOCUMENTS

| | | | | |
|---|---|---|---|---|
| 3,274,124 | A | 9/1966 | O'Hara | 252/451 |
| 3,909,450 | A | 9/1975 | O'Hara | 252/438 |
| 4,988,659 | A | 1/1991 | Pecoraro | 502/235 |
| 6,252,095 | B1 | 6/2001 | Hayashi et al. | 549/523 |
| 6,521,580 | B2 | 2/2003 | Perry et al. | 510/285 |
| 6,734,133 | B1 | 5/2004 | Weisbeck et al. | 502/119 |
| 7,005,112 | B1 | 2/2006 | Takahashi et al. | 422/186.21 |
| 2005/0123739 | A1 | 6/2005 | Chen-Yang et al. | 428/306.6 |
| 2005/0227863 | A1 | 10/2005 | Choudhary et al. | 502/214 |
| 2006/0169624 | A1* | 8/2006 | Radomyselski et al. | 210/96.1 |
| 2006/0293327 | A1 | 12/2006 | Miura et al. | 514/247 |
| 2007/0000837 | A1 | 1/2007 | Davankov et al. | 210/635 |
| 2008/0083432 | A1* | 4/2008 | Wright et al. | 134/10 |
| 2008/0263781 | A1* | 10/2008 | Damaso et al. | 8/142 |

\* cited by examiner

*Primary Examiner*—Chester T Barry
(74) *Attorney, Agent, or Firm*—Arthur E. Gooding

(57) ABSTRACT

An adsorbent for removal of impurities from silicone based solvents is presented. The adsorbent is regenerable for repeated use in cleaning silicone based solvents.

7 Claims, 2 Drawing Sheets

PROCESS FOR REMOVING CONTAMINANTS FROM SILICONE-BASED SOLVENTS

CROSS-REFERENCE TO RELATED APPLICATION

This application is a Division of application Ser. No. 11/130,649 filed May 17, 2005, now U.S. Pat. No. 7,329,624, which is a Continuation-In-Part of application Ser. No. 10/918,880 filed Aug. 16, 2004, now U.S. Pat. No. 7,431,843, and which are incorporated by reference in their entirety

FIELD OF THE INVENTION

The present invention relates to adsorbents in the use of purifying used silicone-based solvents that are used in the dry cleaning process.

BACKGROUND OF THE INVENTION

In the dry cleaning process, clothing or other fabrics to be cleaned are contacted with a solvent that removes dirt, oil and other substances from the clothing. This is a method of removing substances that are on fabrics that are not amenable to removal with aqueous based cleaning detergents. After cleaning the clothing and/or fabrics, the solvent is processed to remove the contaminants that were removed from the clothing, such that the solvent is recycled.

A prominent dry cleaning solvent is perchloroethylene. However, perchloroethylene is an environmental and health hazard, substitute solvents have been developed for use in the dry cleaning process. There has been increasing pressure on the Dry Cleaning industry to use alternatives to perchloroethylene that are more environmentally friendly. This has led to the development of new dry cleaning solvents, such as one group of solvents based on silicone, or siloxanes. One particular solvent has been developed by General Electric is decamethylcyclopentasiloxane, also known as D5. In addition, the new solvent delivers superior fabric quality. This has led to the conversion of about 400 dry cleaning sites from perchloroethylene to the solvent D5.

Today, D5 solvent recovery systems typically use a batch-mode distillation process to purify the solvent. The distillation process is expensive and requires daily, manual intervention to clean the bottom of the distillation apparatus. Improvements in the methods of purifying and recycling cleaning solvents can save energy and money.

SUMMARY OF THE INVENTION

The invention comprises adsorbents for use in removing contaminants from silicone-based solvents. The solvents are chosen for their ability to adsorb a broad spectrum of materials that make up contaminants accumulated in silicone-based solvents used in the dry cleaning industry. The adsorbents are regenerable high surface area materials having pores from about 0.2 nm to about 40 nm. They are selected from materials including inorganic oxides, aluminas, silicas, silica-aluminas, zeolites, alumina-zeolites, molecular sieves and mesoporous crystalline materials.

In one embodiment, the adsorbents are materials that can withstand temperatures up to 600° C. without degradation, for undergoing thermal regeneration of the adsorbents.

It is another embodiment that the adsorbent is a combination of adsorbent materials, where one adsorbent material is for adsorbing polar compounds, and a second adsorbent material is for adsorbing non-polar compounds.

Additional objects, embodiments and details of this invention can be obtained from the following detailed description of the invention.

DETAILED DESCRIPTION OF THE INVENTION

Figure 1:
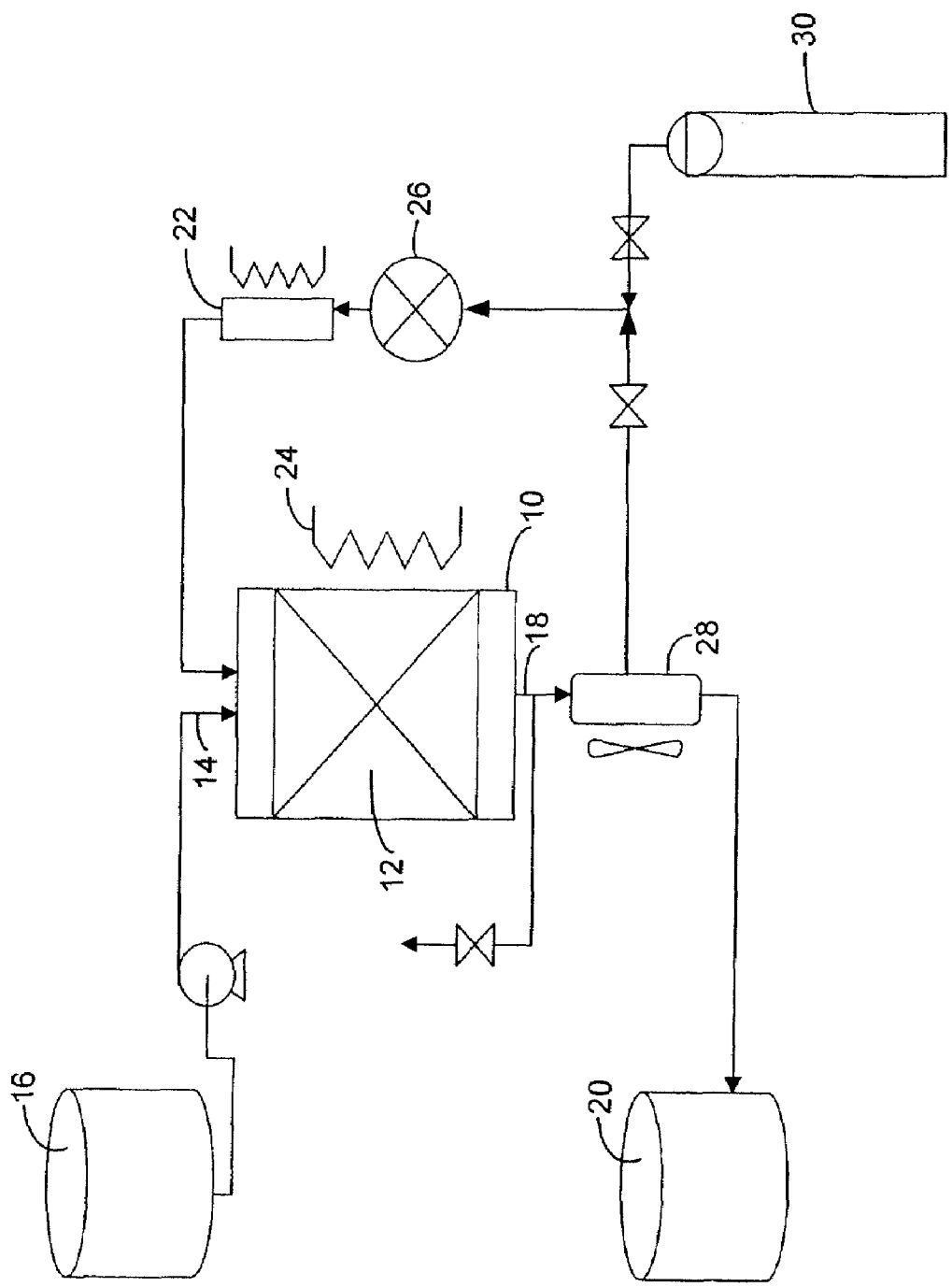
FIG. 1 is an apparatus for performing solvent regeneration.

Replacement cleaning solvents for perchloroethylene include silicone-based compounds that are volatile cyclic, linear or branched siloxane compounds. Examples of these siloxane compounds include, but are not limited to, hexamethyldisiloxane, octamethyltrisiloxane, decamethyltetrasiloxane, dodecamethylpentasiloxane, tetradecamethylhexasiloxane or hexadecamethylheptasiloxane or methyltris (trimethylsiloxy) silane, octamethylcyclotetrasiloxane (D4), decamethylcyclopentasiloxane (D5), dodecamethylcyclohexasiloxane, and tetradecamethylcycloheptasiloxane. Further description of these compounds is found in U.S. Pat. No. 6,521,580, issued on Feb. 18, 2003, and is incorporated by reference in its entirety.

After use of the cleaning in the dry-cleaning process, a typical average single cycle contamination level is 0.3% (or 3000 ppm) by weight. The contaminants generally fall into four major types of solvent soluble contaminants. They are surfactants, that make up to about 50% to 75%; fatty acids, that comprise about 10% to 20%; glycerides that comprise about 10% to 20%; and non-polar compounds, such as waxes, and hydrocarbons, which comprise about 5% to 20%. This list is not meant to be comprehensive, but is only representative of the make up of contaminants found in a dry cleaning solvent after a cleaning cycle.

The removal of contaminants from the silicone-based solvents allows for recycling and reduces the amount of solvents that need to be disposed of. Using adsorbents provides an economical method of removing contaminants, and adsorbents that are regenerable are preferred.

A variety of adsorbents were chosen for testing to learn the properties of the adsorbents relative to the contaminants to be removed from the silicone-based solvents including one or more of inorganic oxides, silicas, aluminas, silica-aluminas, zeolites, alumina-zeolites, molecular sieves, high surface area carbons, and mesoporous crystalline materials. It should be noted that the term silica-alumina does not mean a physical mixture of silica and alumina but means an acidic and amorphous material that has been cogelled or coprecipitated. In this respect, it is possible to form other cogelled or coprecipitated amorphous materials that will also be effective as adsorbents. These include silica-magnesias, silica-zirconias, silica-thorias, silica-berylias, silica-titanias, silica-alumina-thorias, silica-alumina-zirconias, aluminophosphates, mixtures of these, and the like. Preferably, the adsorbents will be selected from one or more of silicas, activated aluminas and molecular sieves. The silicas that are preferred are silylated silicas where the surfaces of the particles have been treated to increase the surface hydrophobicity of the silicas. Silylating treatments are known in the art, and can be found, for example, in U.S. Pat. No. 6,252,095 B1 and U.S. Pat. No. 6,734,133 B1 which are incorporated by reference in their entireties.

The preferred adsorbents are high surface area materials with pore diameters in the range from about 0.2 nm to about 40 nm, and comprising materials that are regenerable. To be regenerable, the materials need to be resistant to high temperatures and/or resistant to degradation from exposure to solvents for removing the contaminants adsorbed from the silicone-based solvents. It is desirable that the adsorbents withstand temperatures up to at least 600° C. to enable the volatilization of the adsorbed contaminants.

The adsorbents can be further improved by optimizing the adsorbent acidity. The acidity can be controlled through ion exchange to deposit metals such as alkali or alkaline earth metals on the adsorbent. Preferred metals include potassium, sodium, cesium, magnesium and calcium.

In regenerating the adsorbents, recovery of residual silicone solvent is a consideration. The solvent may be recovered by a low level of heating at a temperature insufficient to drive off the contaminants from the adsorbent. However, there are some contaminants with low boiling points and can be driven off with the silicone solvent during a solvent recovery stage. When there are contaminants removed with the residual solvent, the recovered solvent can be collected and further treated for separating a smaller amount of solvent from the contaminants, including distillation of the recovered solvent or treatment with a second adsorbent that The contaminants in the silicone-based solvents include polar materials and non-polar materials. Often adsorbents will preferentially remove either polar materials or non-polar materials. Since the contaminants often encompass both types of materials, the adsorbents for removing the contaminants can comprise a mixture of adsorbents, wherein at least one of the adsorbents adsorbs polar compounds, and at least one of the adsorbents adsorbs non-polar compounds. Since the composition of contaminants is predominantly polar compounds, such as surfactants and fatty acids, the mixture of adsorbents preferably comprises a mixture having at least 50% polar adsorbing adsorbent. Ranges of mixtures include an adsorbent for polar compounds making up from between 50% to 99% of the mixture by weight, and an adsorbent for non-polar compounds making up from between 1% and 50% of the mixture by weight.

The choice of adsorbent for use in removing contaminants is one that is regenerable, and one method of regeneration of the adsorbent is to heat the adsorbent to volatilize contaminants, or to oxidize the contaminants to volatile oxidized molecules. To improve the ability to oxidize contaminants, the adsorbents can be optionally loaded with small amounts of metals for catalyzing oxidation reactions. Metals deposited include transition elements and non-transition metals. These elements include scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), gallium (Ga), germanium (Ge), indium (In), thallium (Tl), tin (Sn), lead (Pb), antimony (Sb), bismuth (Bi) and polonium (Po). Preferably, the elements are selected from a smaller group of elements comprising ruthenium, rhodium, palladium, rhenium, osmium, iridium and platinum. The elements should be sparsely distributed on the adsorbent so as to not interfere with the primary purpose of adsorbing the contaminants.

The adsorbents can be regenerated for re-use. In one embodiment, the process for regenerating the adsorbents includes draining the adsorbent chamber of any silicone solvent, and heating the chamber to a temperature to recover any residual solvent. The adsorbent is heated to a higher temperature level to volatilize the contaminants adsorbed onto the adsorbent. Volatilization can include passing an oxidizing gas over the adsorbent to oxidize contaminants and removing the oxidized products of the contaminants.

EXAMPLE

A variety of adsorbents were tested covering a range of parameters. Among the tested adsorbents were:

activated carbons with different surface areas, and different porosities;

alumina with different surface areas, and different porosities;

silica gel with different surface areas, and different porosities;

zeolites with different structures and pore sizes; and mesoporous materials, such as MCM-41.

A desirable feature of mesoporous materials is the greater range of pore sizes which allows for the adsorption of larger molecules that might be present as contaminants in the solvent. The mesoporous materials include crystalline mesoporous materials, and non-crystalline amorphous mesoporous materials. The tradeoff with larger pored materials is that there is generally a lower surface area per gram of material and can lead to fewer passes of the solvent before regeneration is required.

A summary of the results of the use of various adsorbents shows the removal of impurities from the D5 solvent.

TABLE 1

| Adsorbent Description | Surfactant removal, % | Fatty Acids removal, % | Tri-glycerides removal, % | Hydrocarbons Removal, % |
|---|---|---|---|---|
| Darco MRX | 96.69 | 93.1 | 90.85 | 88.05 |
| LECO Carbon | 76.53 | 87.61 | 85.34 | 51.94 |
| CaCO$_3$ | 13.91 | 6.9 | 15.66 | −0.85 |
| Calgon Carbon | 91.57 | 95.04 | 91.52 | 96.35 |
| BaKX | 14.41 | 60.54 | −14.89 | 0 |
| KY | 83.04 | 95.64 | 13.75 | 5.64 |
| Aldrich SiO$_2$ | 97.93 | 91.45 | 92.74 | 0 |
| Vasken SiO$_2$ | 96.11 | 90.75 | 92.58 | 0 |
| SORBPLUS | 40.47 | 91.9 | −2.91 | 0 |
| A-201 | 97.06 | 94.18 | 90.68 | −0.59 |
| A-204-1 | 88.9 | 99.25 | 96.43 | 0 |
| AZ-300 | 95.36 | 99.23 | 97.5 | 29.01 |
| S-115 | 0.55 | 63.34 | −1.8 | 0 |
| TMC SiO$_2$ | 3.16 | 3.6 | 2.22 | 0 |
| F-Silicalite | 10.4 | 86.31 | 7.28 | 0 |
| R-gCB | 79.72 | 98.69 | 53.25 | 0 |
| MFI | 38.81 | 87.54 | 2.94 | 0 |
| MCM-41 | 92.16 | 98.97 | 97.9 | 0 |
| 13X | 86.66 | 95.69 | 32.77 | 0 |

The preferred adsorbents include, but are not limited to, high surface area carbons, aluminas, silica gel, zeolites, mesoporous alumina, and combinations of these adsorbents. Examples of preferred adsorbents include high surface area carbons such as Darco MRX and Calgon carbon, silicas (SiO$_2$) by Aldrich or Vasken, and commercial adsorbents such as A-201, A-204-1, AZ-300 and MCM-41.

A-201 and A-204-1 are a spherical activated alumina with a high surface area. AZ-300 is a spherical alumina-zeolite composite with low reactivity. These are commercially available alumina adsorbents produced by UOP. They can be regenerated for re-use by purging of evacuating at an elevated temperature.

MCM-41 is a mesoporous crystalline material obtained by a templating mechanism with an exceptionally high porosity. To some degree it has an ordered structure such that there are non-intersecting channels. By changing the length of the template molecure, the width of the channels can be controlled to be within the range from 2 to 10 nm. The walls of the channels are amorphous silica. This feature, together with its exceptional porosity, up to 80%, makes MCM-41 a desirable candidate for adsorbing large amounts of contaminants.

Other materials selected and useful as adsorbents for removing contaminants include mesoporous materials such as, but not limited to, Y-85 zeolite, LZ-210, SN-LZ-210, AW-LZ-15, and Y zeolite based hydrocracking catalysts.

Process and Apparatus for Regeneration

The adsorbents are regenerated to further improve the economics of solvent cleaning and regeneration.

An apparatus for cleaning the solvent and regenerating the adsorbent is shown in FIG. 1. The apparatus comprises an adsorbent chamber 10 for holding an adsorbent 12. The solvent enters the adsorbent chamber 10 through an inlet 14, directed from a contaminated solvent supply source 16. Typically, the supply 16 is a holding tank for receiving contaminated solvent from dry cleaning establishments, and the solvent is pumped to the adsorbent chamber 10. The contaminated solvent passes over the adsorbent 12 wherein the impurities in the solvent are removed generating a regenerated solvent effluent stream. The solvent effluent stream exits the adsorbent chamber through an exit 18 and is collected in a storage tank 20 for later redistribution to dry cleaning establishments.

The apparatus further comprises a heating unit 22 for generating a heated gas to pass over the adsorbent 12. The heater 22 can be a two stage heater for generating a hot gas at two different temperature levels, or optionally, the apparatus includes a second heater 24 for providing heat at a second higher level. In one configuration of the present invention, the apparatus includes a recirculation blower 26 for recirculating hot gas over the adsorbent 12. The apparatus further includes a condensing unit 28 for recovering vaporized solvent from the adsorbent 12. The apparatus further comprises a source of gas 30 that can be passed over the adsorbent 12 during the second stage of heating.

Figure 2:
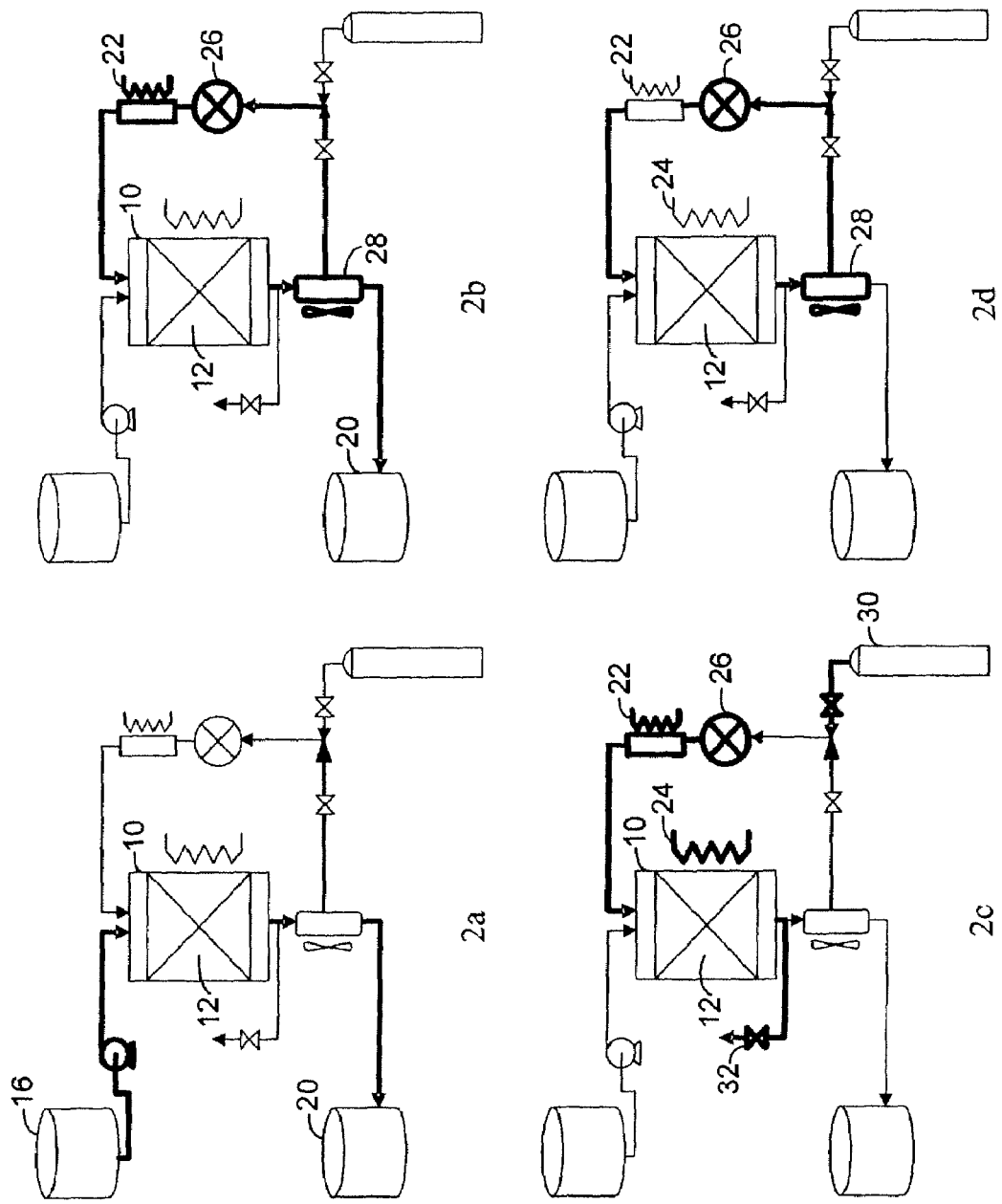
FIGS. 2a-d are steps in the regeneration process for regenerating that purifying adsorbent.

The process of regenerating the solvent is shown in FIG. 2a, and entails passing the solvent with contaminants, from a supply 16, over the adsorbent 12 in an adsorbent chamber 10 to remove the contaminants, generating a solvent effluent stream relatively free of impurities, and passing the effluent stream to a holding tank 20. Preferably, the impurities are reduced to a level of less than or equal to 500 ppm by weight (<0.05%). The process continues until the concentration of contaminants in the solvent leaving the adsorbent chamber exceeds a preselected value.

Upon reaching the preselected value of impurities in the solvent effluent stream, the flow of solvent to the adsorbent bed 12 is discontinued and the adsorbent chamber 10 is drained of all remaining solvent. The regeneration of the adsorbent entails several considerations. One consideration is the recovery of residual solvent from the adsorbent during the regeneration process. A second consideration is the convenient removal of impurities from the adsorbent.

To address these considerations, the regeneration of the adsorbent entails a two stage heating process for the regeneration of the adsorbent. A first stage heating of the adsorbent is at a temperature sufficient to remove any excess solvent from the adsorbent. The first stage heating step consists of heating the adsorbent in the adsorbent chamber to a temperature from about 150° C. to about 300° C., and preferably about 200° C. A preferred method is shown in FIG. 2b, where the excess solvent remaining in the adsorption chamber is vaporized and carried out in a gaseous phase in an effluent gas stream until the adsorbent 12 is dried. After the adsorbent chamber 10 is drained, a gas is heated by a heater 22, and passed through the adsorbent chamber 10, generating an effluent gas stream. The effluent gas stream is passed through a condenser 28 and the solvent in the effluent gas stream is condensed and recycled to a storage tank 20. The heated gas is recycled with a recirculation blower 26, and passed through the heater 22. The first stage is continued until the desired recovery of solvent is obtained. During the first stage heating, the gas used will preferably comprise a non-oxidizing gas, such as for example nitrogen, argon, or carbon dioxide.

The condensing unit 28 can be an air cooled heat exchanger, or depending on the load requirements, can be another type of condensing unit.

The first stage heating can be performed in a number of ways. One method of heating is to pass a hot gas heated to a temperature of about 200° C. over the adsorbent. The hot gas vaporizes the solvent and carries the gaseous solvent out of the adsorbent chamber. Another method of heating involves using a heater attached to the adsorbent chamber. The heater can be an electric heater, a tube and fin heat exchanger with a hot fluid passing through the tubes, or any other type of heating unit capable of heating the adsorbent to a temperature from about 150° C. to about 300° C.

After the desired recovery of solvent is obtained, the second stage heating further heats the adsorbent, as shown in FIG. 2c. The adsorbent is further heated to a greater temperature to remove the contaminants remaining on the adsorbent. It has been found that the contaminants are desorbed, or burned off, from the adsorbent at temperatures in the range of about 400° C. to about 600° C. Preferably, the temperature is in the range from about 450° C. to about 500° C. A gas is supplied from a source 30 and heated through the heater 22. The heated gas passes over the adsorbent 12 and picks up contaminants on the adsorbent 12. The heated gas with contaminants is then vented 32 or passed to other units for processing, depending on the degree of removal needed. Optionally, the gas is heated to an initial temperature, and a second heater 24 located in, or around, the adsorbent chamber 10 heats up the adsorbent 12 to a temperature sufficient to desorb the contaminants, or to decompose the contaminants to volatile compounds that are removed in the gas stream. During the second stage heating, the gas will preferably comprise an oxidizing gas, such as for example air, or oxygen.

One method of removing the impurities, or contaminants, from the adsorbent is to pass a heated gas that oxidizes the impurities, and creates a volatile oxidized product that is removed in the gas stream. Another method for removing impurities comprises using steam to desorb, or decompose the impurities on the adsorbent 12.

The vented gas containing the impurities can also be passed through a filter to trap volatile organic compounds, or to remove other harmful impurities that might be generated by the thermal decomposition of the adsorbed contaminants.

The final step in the process is shown in FIG. 2d, wherein the adsorbent 12 is cooled down to a temperature after the impurities have been removed. Gas is recirculated by a recirculation blower 26, and passed over the adsorbent 12. The gas is cooled by the condensing unit 28 to remove heat picked up from passing over the adsorbent 12. Following the cooling step, the adsorption process is repeated to process the solvent.

The process is repeatable, and can be performed for about 50 cycles before considering replacing the adsorbent.

The apparatus may further be expanded to have multiple adsorbent beds 12. The process can use one or more adsorbent beds while one or more adsorbent beds are undergoing regeneration of the adsorbent. An apparatus with multiple adsorbent beds 12 would not require duplication of other components in the apparatus, such as the gas heater 22, recirculation blower 26, and condensing unit 28. The use of multiple adsorbent beds can allow for continuous processing of the contaminated solvent.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. The process of removing contaminants from silicone-based solvents comprising:
    contacting the solvent with an adsorbent, wherein the adsorbent removes contaminants to a level of less than 300 ppm by weight, wherein the contaminants are selected from the group consisting of surfactants, fatty acids, triglycerides, diglycerides, monoglycerides, waxes, paraffins, hydrocarbons, wax esters, cholesterol esters, squalene and mixtures thereof; and
    regenerating the adsorbent at regeneration conditions.

2. The process of claim 1 wherein the adsorbent removes contaminants to a level of less than 100 ppm by weight.

3. The process of claim 1 wherein the adsorbent is selected from the group consisting of inorganic oxides, aluminas, silicas, silica-aluminas, zeolites, alumina-zeolites, molecular sieves, mesoporous crystalline and non-crystalline amorphous materials, and mixtures thereof.

4. The process of claim 1 wherein the adsorbent is regenerated through heating to a temperature between about 300° C. and about 600° C.

5. The process of claim 4 wherein an oxidizing gas is passed over the heated adsorbent.

6. The process of claim 1 wherein the adsorbent is regenerated by contacting the adsorbent with a second sorbent to remove the contaminants.

7. The process of claim 1 wherein the adsorbents are ion exchanged to contain a metal selected from the group consisting of sodium, potassium, cesium, magnesium, calcium, and mixtures thereof.

* * * * *